(12) United States Patent
Iwahashi

(10) Patent No.: US 8,905,936 B2
(45) Date of Patent: Dec. 9, 2014

(54) CATHETER HAVING A BIASING MEMBER

(75) Inventor: Shigenobu Iwahashi, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 64 days.

(21) Appl. No.: 13/449,864

(22) Filed: Apr. 18, 2012

(65) Prior Publication Data

US 2012/0271174 A1    Oct. 25, 2012

(30) Foreign Application Priority Data

Apr. 19, 2011    (JP) .................. 2011-093232

(51) Int. Cl.
| | |
|---|---|
| *A61B 8/14* | (2006.01) |
| *A61B 8/00* | (2006.01) |
| *A61B 6/00* | (2006.01) |
| *A61B 5/00* | (2006.01) |
| *A61B 8/12* | (2006.01) |
| *A61B 8/08* | (2006.01) |

(52) U.S. Cl.
CPC ............... *A61B 8/12* (2013.01); *A61B 5/0073* (2013.01); *A61B 8/4461* (2013.01); *A61B 5/0084* (2013.01); *A61B 8/445* (2013.01); *A61B 8/483* (2013.01)

USPC ........... 600/467; 600/437; 600/466; 600/462; 600/478

(58) Field of Classification Search
USPC ......... 600/466, 467, 437, 459, 476, 462, 473, 600/478, 342; 385/116, 117
See application file for complete search history.

(56) References Cited

U.S. PATENT DOCUMENTS

| | | | | |
|---|---|---|---|---|
| 5,925,055 | A * | 7/1999 | Adrian et al. | ........... 606/159 |
| 6,258,052 | B1 * | 7/2001 | Milo | ........... 604/22 |
| 7,654,985 | B2 * | 2/2010 | Dinsmoor et al. | ........... 604/174 |
| 2009/0209855 | A1 * | 8/2009 | Drilling et al. | ........... 600/435 |

FOREIGN PATENT DOCUMENTS

JP         2004-97286 A    4/2004

* cited by examiner

*Primary Examiner* — Katherine Fernandez
(74) *Attorney, Agent, or Firm* — Buchanan Ingersoll & Rooney PC

(57) ABSTRACT

A catheter includes a catheter main body provided with a window portion through which an inspection wave passes, a drive shaft provided with a detection unit detecting the inspection wave and concurrently installed advanceably and retractably in an axial direction inside the catheter main body, and a bias member biasing a force onto the drive shaft for moving the drive shaft forward toward the distal side thereof.

18 Claims, 9 Drawing Sheets

CATHETER HAVING A BIASING MEMBER

CROSS REFERENCES TO RELATED APPLICATIONS

The present invention contains subject matter related to Japanese Patent Application JP2011-093232 filed in the Japanese Patent Office on Apr. 19, 2011, the entire content of which is incorporated herein by reference.

TECHNICAL FIELD

The present invention generally pertains to a catheter. More particularly, the invention relates to a catheter used for diagnosis of a living-body lumen such as a blood vessel, a vascular channel and the like.

BACKGROUND DISCUSSION

To treat a stenosis portion or an occlusion portion inside a living-body lumen such as a blood vessel, a vascular channel and the like, in order to observe living-body properties inside the lumen or observe the state after treatment, there is used a catheter for diagnosis, which obtains an image of a living-body lumen by utilizing an inspection wave such as ultrasound, light or the like. An example of such a catheter is disclosed in Japanese Unexamined Patent Publication No. 2004-97286.

This kind of catheter includes a catheter main body provided with a window portion through which an inspection wave passes, and a drive shaft which is provided with a detector for transmitting & receiving the inspection wave and concurrently, which is installed advanceably and retractably in the axial direction inside the catheter main body. Then, while moving back, that is, by pulling back the drive shaft toward the proximal side inside the catheter, the inspection wave is transmitted & received by the detector.

However, when an operation such as insertion into a blood vessel or the like is carried out erroneously in a state in which the drive shaft remains pulled back, a defect such as a kink or the like can occur at a portion not supported by the drive shaft. When kinking or the like occurs, replacement of the catheter becomes necessary.

SUMMARY

According to one aspect, a catheter disclosed here includes a catheter main body provided with a window portion through which an inspection wave passes; a drive shaft provided with a detection unit detecting the inspection wave and concurrently installed advanceably and retractably in an axial direction inside the catheter main body; and a bias member biasing a force onto the drive shaft for moving the drive shaft forward toward the distal side thereof.

According to another aspect, a catheter is positionable in a living body lumen to transmit and receive inspection waves to form an image of tissue in a living body lumen, wherein the catheter comprises: a catheter main body; a detection unit positioned in the catheter and configured to detect the inspection waves and output signals based on the inspection waves detected by the detection unit; with the catheter main body possessing a distal end portion at which is located a window portion configured to permit the inspection waves to pass through to be detected by the detection unit, and the detection unit being axially positionable in the catheter main body to detect the inspection waves passing through the window portion; and a signal line connected to the detection unit to transmit the signals from the detection unit. A drive shaft is positioned in the catheter main body and is operatively connectable to an external drive apparatus to move the drive shaft rotationally and axially in a distal direction and a proximal direction, with the drive shaft possessing a distal end to which the detection unit is fixed so that the detection unit moves axially and rotationally together with the drive shaft. A bias member biases the drive shaft in the distal direction so that if the drive shaft is unintendedly move in the proximal direction, the drive shaft is automatically moved toward the distal direction by the biasing member.

The catheter is constructed in such a way that even in a case in which the drive shaft is erroneously moved backward in the proximal direction, the drive shaft moves forward toward in the distal direction by a force of the bias member when releasing the backward movement of the drive shaft. Consequently, it is possible to inhibit or prevent a situation from occurring in which the drive shaft is maintained to be moved backward inside the catheter main body and so it is possible to avoid a situation in which a defect such as kink or the like occurs at the catheter main body.

DETAILED DESCRIPTION

Figure 1:
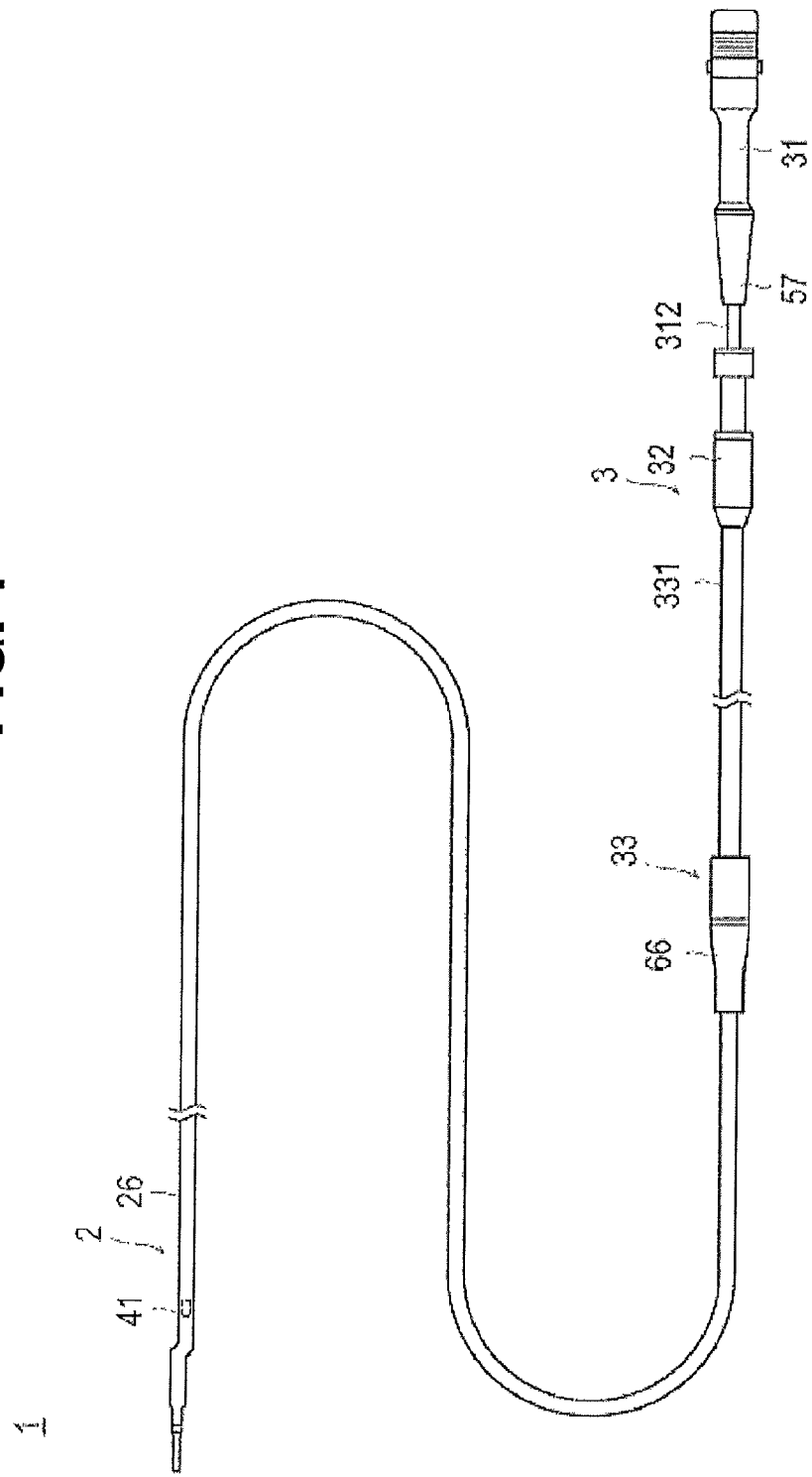
FIG. 1 is a somewhat schematic side view of an embodiment of a catheter disclosed here by way of example.

Set forth below is a detailed description of examples of embodiments of the catheter disclosed here. The detailed description which follows describes features and aspects of the catheter with reference to the drawing figures. For convenience of explanation, the size ratio of the drawings is exaggerated, is different from the actual ratio and is not necessarily intended to be an accurate illustration of the relative dimensions of parts and features of the catheter.

With reference to FIG. 1, the catheter 1 disclosed here has useful application as a tool to diagnose the inside of a living body lumen through insertion inside the living body lumen such as a blood vessel, a vascular channel and the like. The catheter includes a catheter main body 2 having a long shape (elongated) and exhibiting flexibility, and a steering unit 3 at the proximal side of the catheter main body 2 and which is arranged on the hand side of an operator. The steering unit 3 is configured so as not to be inserted into the living body lumen in order for the operator to steer it. In the description below, the side or end of the catheter 1 inserted into the living body lumen is referred to as the distal side or distal end, and the side of the catheter not inserted into the living body lumen is referred to as the proximal side or proximal end.

Figure 6:
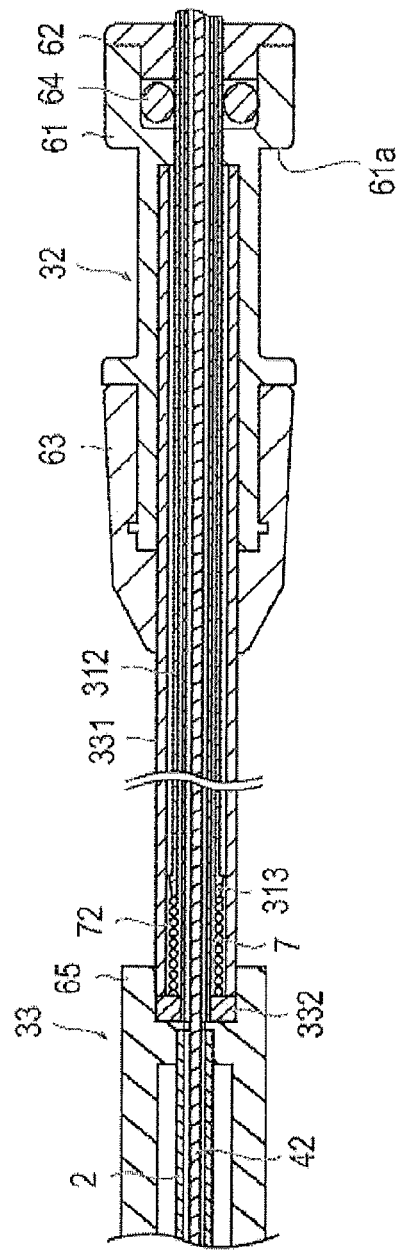
FIG. 6 is a lengthwise-direction cross-sectional view of the unit connector and a relay connector.
Figure 7:
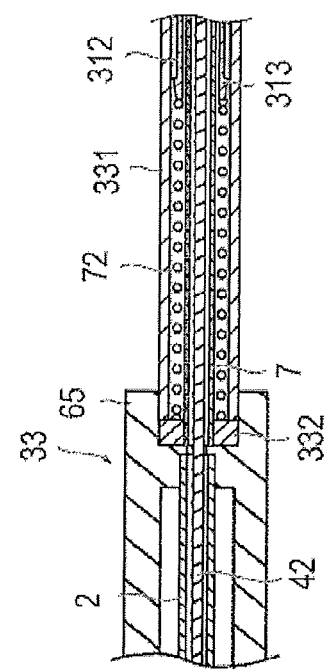
FIG. 7 is a cross-sectional view of a portion of the connector shown in FIG. 6 illustrating the bias member.

The catheter 1 according to this first embodiment includes the catheter main body 2 having a window portion 26 through which an inspection wave passes and a transducer unit 41 (i.e., detection unit) for detecting the inspection wave. The catheter also comprises a drive shaft 42 arranged for advancing movement and retracting movement in the axial direction inside the catheter main body 2 and a bias member 72 (see FIG. 6) for applying a biasing force to the drive shaft 42 which urges or moves the drive shaft 42 in the forward direction toward the distal end. When the inspection wave is detected by the transducer unit 41, the drive shaft 42 moves backward against the biasing force of the bias member 72, toward the proximal end. The catheter 1 further includes a hub 31 to which a proximal portion of the drive shaft 42 is connected; an inner tube 312 (constituting an example of a first tube body) whose proximal portion is fixed to the hub 31, which extends toward in the distal direction from the hub and concurrently, through which the drive shaft 42 passes; a relay connector 33 (constituting an example of a first connector unit) connected to the catheter main body 2; and a support tube 7 (constituting an example of a second tube body) whose distal portion is fixed on the relay connector 33, which extends in the proximal direction, concurrently, through which the drive shaft 42 passes and which is inserted in a nested manner between the inner tube 312 and the drive shaft 42 (the drive shaft, the support tube 7 and the inner tube 312 axially overlap one another as shown in, for example, FIG. 6). The bias member 72 is thus positioned radially outwardly of the support tube 7 as shown in FIGS. 6 and 7. The bias member 72 is arranged to cover the support tube 7 and also to apply a bias (tensile) force between the inner tube 312 and the relay connector 33 (see FIG. 6 and FIG. 7). Further details will be explained below.

Figure 2:
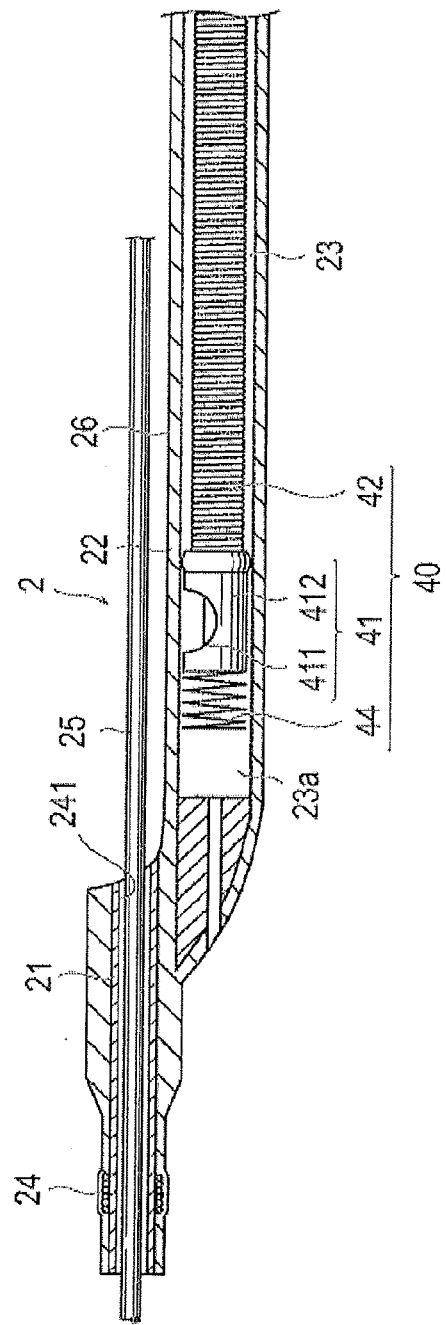
FIG. 2 is a lengthwise-direction cross-sectional view of the distal portion of the catheter main body.

As shown in FIG. 2, a catheter main body member 22 having a hollow shape of the catheter main body 2 extends and protrudes toward the distal end and also is bonded to a guide wire insertion portion 21 so as to cover the guide wire insertion portion 21 through which a guide wire 25 passes at a distal portion of the catheter main body 2. The guide wire insertion portion 21 is arranged such that the center axis of the guide wire insertion portion 21 is eccentric with respect to the center axis of the catheter main body 2.

A marker 24 is arranged on the distal side of the guide wire insertion portion 21. The marker 24 permits confirmation of the distal end position of the catheter 1 under X-ray illumination when inserted in a living body lumen. The marker 24 has a contrast property under X-ray illumination by having X-ray impermeability, and such a marker 24 usually has a contrast property also in a CT scan, so that it can be used also in a CT scan.

At the guide wire insertion portion 21, there is formed a guide wire lumen 241 which passes through along the axial direction of the catheter main body 2. The guide wire 25 is inserted into this guide wire lumen 241 and passes through the guide wire lumen 241. The guide wire 25 is inserted beforehand as far as the vicinity of the target lesion inside the living body before inserting the catheter 1 inside the living body, and the guide wire is used to guide the catheter 1 as far as the target portion such as, for example, the target lesion.

In the catheter main body 2, there is formed a working lumen 23 which extends along the lengthwise or axial direction of the catheter main body member 22. This working lumen 23 is a hollow path in which an imaging core 40, described in more detail later, is slidably incorporated in the axial direction of the catheter main body 2.

The tube wall of the catheter main body 2, at a position on the proximal side of the guide wire insertion portion 21, is provided with a window portion 26 which permits transmission of an inspection wave such as light, ultrasound or the like. The catheter 1 according to this embodiment disclosed as an example is a catheter for obtaining images by an ultrasound signal utilizing an intravascular ultrasound (IVUS) image diagnosis catheter and it is possible to obtain cross-sectional images by transmitting & receiving the ultrasound (inspection wave) through the window portion 26.

The imaging core 40 is provided with a transducer unit 41 having a construction that includes an ultrasonic transducer 411 for transmitting & receiving ultrasound toward a tissue within a living body lumen housed inside a housing 412, a drive shaft 42 whose distal end is equipped with the transducer unit 41 and concurrently which transmits a rotational moving force, and a rotation stabilizing coil 44 mounted on the distal side of the transducer unit 41.

The ultrasonic transducer 411 is fixed to the distal end of the drive shaft 42 which can carry out advancing and retraction operation inside the working lumen 23. There is no limitation on the fixing method that can be used to fix ultrasonic transducer 411 is fixed to the distal end of the drive shaft 42. As an example, it is possible to bond the transducer by an adhesive agent or by soldering.

The housing 412 of the transducer unit 41 possesses a tubular shape in which the distal end of the housing 412 is closed, and the proximal end is fixed on the drive shaft 42. There is no limitation for the fixing method and, for example, it is possible to bond the housing by an adhesive agent or by soldering. The housing 412 includes an opening portion which is formed by notching a portion corresponding to the ultrasound transmission and receiving unit of the ultrasonic transducer 411.

The drive shaft 42 is configured to be flexible and also capable of transmitting a rotational motion power generated in an after-mentioned scanner apparatus 81 (see FIG. 8) to the transducer unit 41. By way of example, the drive shaft 42 is constructed as a tubular body of a multi-layer coil shape such as a three-layer coil whose winding direction is alternated in a manner from right to left and again to the right. Owing to the fact that the drive shaft 42 is able to transmit the rotational motion power, the transducer unit 41 rotates and it is possible to observe 360 degrees of the target lesion inside the living body lumen such as a blood vessel, a vascular channel and the like. Also, a signal line 54 (see FIG. 5) passes through the inside of the drive shaft 42, for transmitting a signal detected by the transducer unit 41 to the steering unit 3.

The rotation stabilizing coil 44 is formed by spirally winding a wire element. The rotation stabilizing coil 44, whose proximal side is fixed on the housing 412, serves as a guide for rotating the ultrasonic transducer 411 stably. The method for fixing the rotation stabilizing coil 44 is not limited. As an example, it is possible to bond it by an adhesive agent or by soldering.

The rotation stabilizing coil 44 is preferably manufactured of a metal material. Examples include an X-ray impermeable metal such as spring steel, stainless steel, super elastic alloy, cobalt-based alloy, gold, platinum, tungsten and the like or an alloy including any of these. It is also possible to manufacture the rotation stabilizing coil 44 using a material other than a metal material.

The steering unit 3 includes, as shown in FIG. 1, a hub 31 which is arranged on the proximal end, a unit connector 32 in which the inner tube 312 connected with the hub 31 is inserted in an advancing and retracting manner, and the relay connector 33 which is connected to the unit connector 32 through the outer tube 331 and concurrently, which connects the catheter main body 2 and the steering unit 3.

Figure 4:
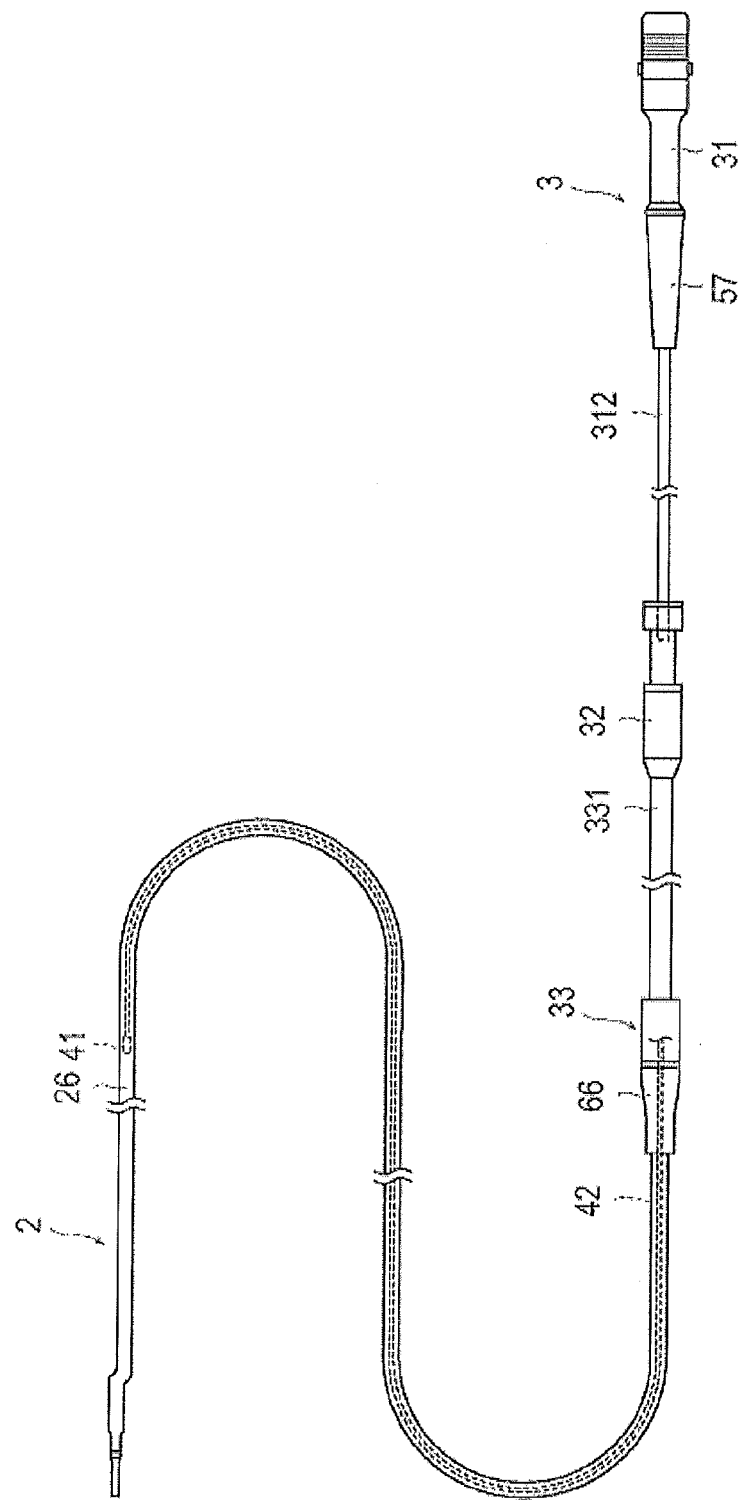
FIG. 4 is a side view of the catheter when pulling out the inner tube maximally from the unit connector.
Figure 5:
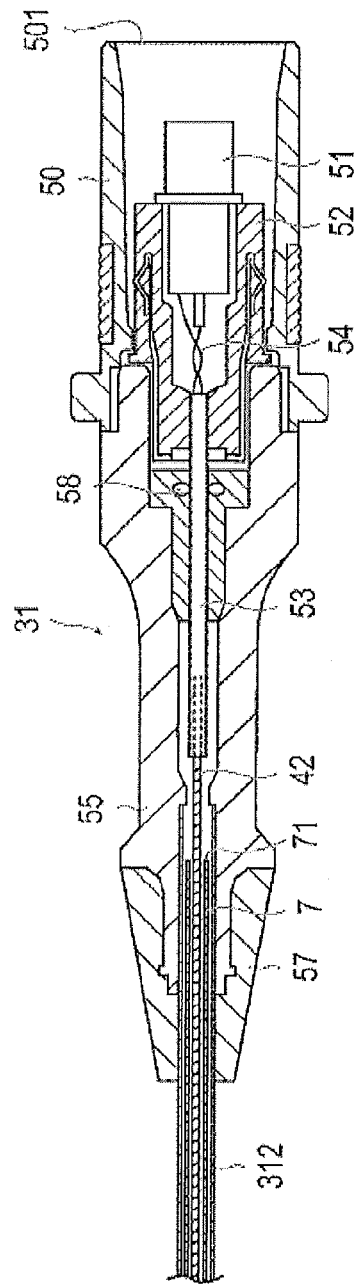
FIG. 5 is a lengthwise-direction cross-sectional view of the hub of the catheter.

The hub 31 holds, as shown in FIG. 5, the drive shaft 42 and the inner tube 312. By pressing the inner tube 312 into the inside of the unit connector 32 and the outer tube 331 or by pulling it out therefrom, the drive shaft 42 cooperatively slides in the axial direction inside the steering unit 3 and the catheter main body 2. Aspects of the movement of the drive shaft 42 by the pressing-in and the pulling-out of the inner tube 312 are as shown in FIG. 3 and FIG. 4.

Figure 3:
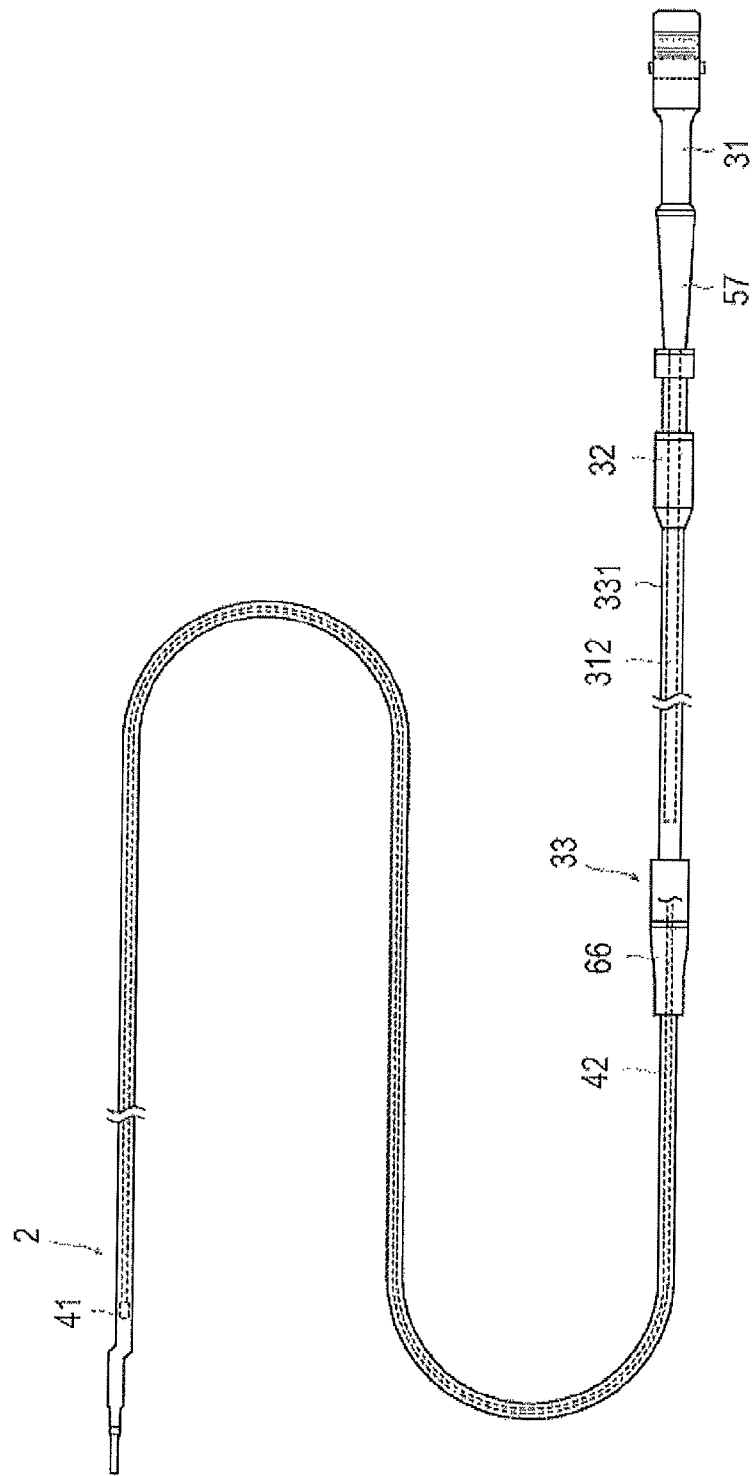
FIG. 3 is a side view of the catheter when pressing an inner tube maximally into a unit connector.

When the inner tube 312 is pressed-in to the maximum extent, as shown in FIG. 3, with respect to the inner tube 312, an end portion thereof on the catheter main body 2 side reaches as far as the vicinity of the catheter main body 2 side end portion of the outer tube 331, more specifically, as far as the vicinity of the relay connector 33. Then, in this state, the transducer unit 41 is positioned in the vicinity of the distal end of the catheter main body member 22 of the catheter main body 2. The distal portion of the anti-kink protector 57 (see FIG. 5) in the hub 31 abuts on the proximal portion of the unit connector 32, thereby stopping the progress of the drive shaft 42. At that time, as shown in FIG. 2, the size of each member is to be set such that a gap 23a forms between the distal end of the imaging core 40 and the distal end of the working lumen 23. The size of the gap 23a can be set to an appropriate size in consideration of the manufacturing tolerance. As an example, the size of the gap can be approximately 2 mm. Even if the drive shaft 42 is made to progress maximally or is pushed-in to the maximum extent, the distal end of the imaging core 40 does not contact the wall surface or the like. Thus, even if the imaging core 40 is rotated in a state in which the drive shaft 42 has been moved to the maximum extent in the forward direction, it is possible to prevent the imaging core 40 from being damaged.

Also when the inner tube 312 is pulled out to the maximum extent, as shown in FIG. 4, with respect to the inner tube 312, a stopper 313 formed at the distal end thereof (see FIG. 6) engages the inner wall of the unit connector 32 and a portion other than the vicinity of the distal end engaged will be exposed. Then, in this state, the transducer unit 41 is positioned at the place located toward the steering unit 3 as much as the amount by which the inner tube 312 is pulled out. The fact that the transducer unit 41 moves while rotating makes it possible to create a three-dimensional tomographic image of a blood vessel, a vascular channel and the like.

The description which follows describes in more detail the construction of each portion of the catheter 1.

Referring to FIG. 5, the hub 31 includes a joint 50, a male connector 51, a rotor 52, a connection pipe 53, a signal line 54, a hub main body 55, an anti-kink protector 57 and a seal member 58 such as an O-ring packing.

The joint 50 includes an opening portion 501 on the user's hand side (proximal end) of the catheter 1 and is constructed so that the male connector 51 and the rotor 52 are arranged on the inside of the joint 50. It is possible for the male connector 51, from the opening portion 501 side of the joint 50, to be interlocked with a female connector included in an external drive apparatus 80 (see FIG. 8) and so mechanical and electrical connections between the external drive apparatus 80 and the male connector 51 become possible.

Figure 8:
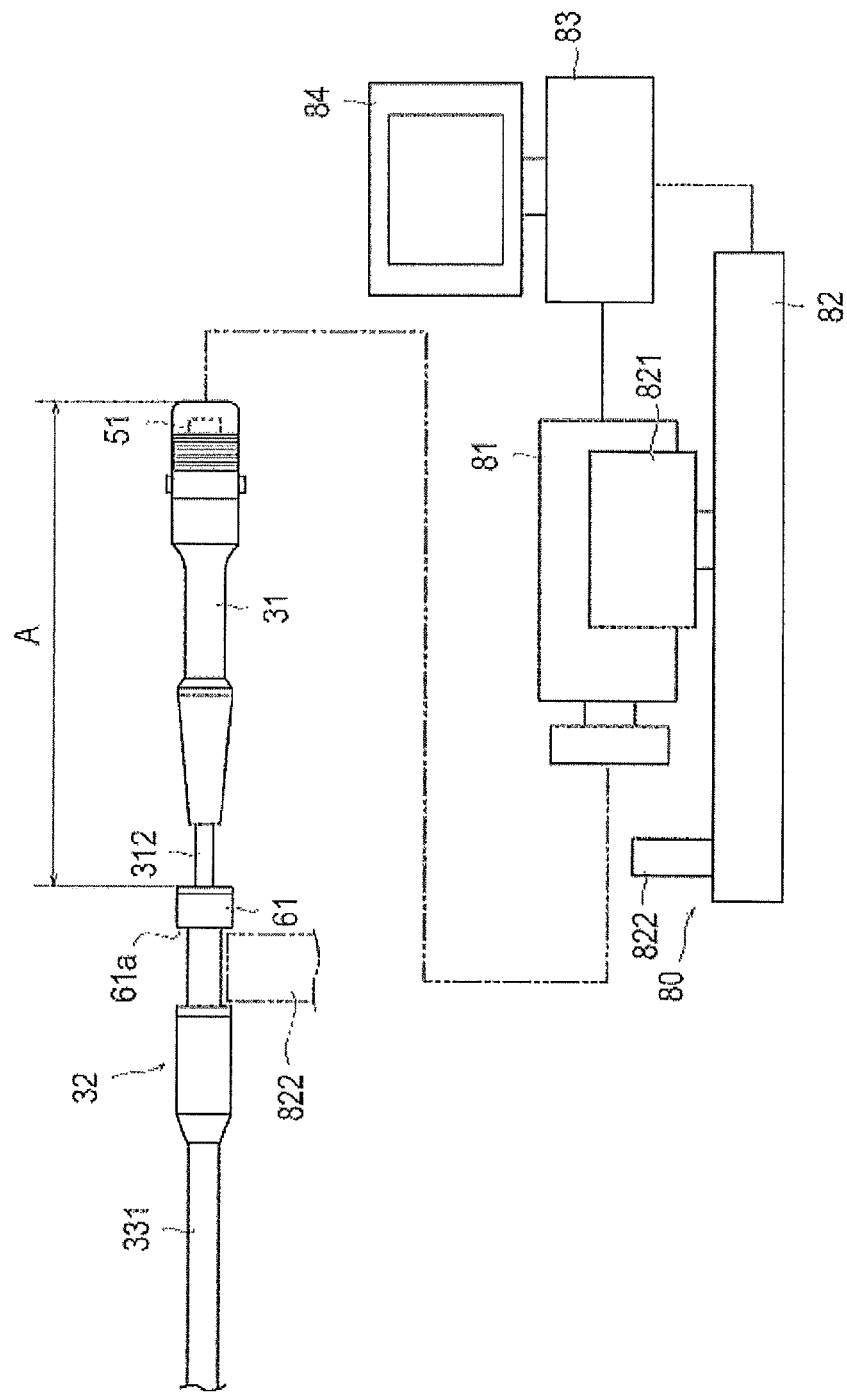
FIG. 8 is a diagram showing a relation between the catheter and an external drive apparatus.

The external drive apparatus 80 includes, as shown in FIG. 8, a scanner device 81 incorporating a drive power supply such as, for example, a motor, an axial direction moving device 82 which holds the scanner device 81 and which causes it to move in the axial direction by, for example, the motor, a control unit 83 for controlling the scanner device 81 and the axial direction moving device 82, and a display unit 84 for displaying an image obtained by the transducer unit 41. The axial direction moving device 82 includes a scanner device hold portion 821 for holding and fixing the scanner device 81, and a catheter support portion 822 for supporting the window portion 26 so as not to deviate from a target portion when moved. The scanner apparatus 81 carries out transmission & reception of a signal from the transducer unit 41 by being connected with the male connector 51 and simultaneously, transmits a drive force by which the drive shaft 42 is rotated. The catheter support portion 822 is fitted into a recess portion 61a at a center portion of the unit connector main body 61 in the unit connector 32. This construction helps ensure that the catheter main body 2 does not move backward together when the hub 31 is moved backward (pulled back). A portion shown by a reference symbol A in FIG. 8 and the imaging core 40 linked with this portion move at the time of the pullback.

A scan utilizing ultrasound in this example of the catheter 1 is carried out by a mechanism of scanning an image which is transmitted and received by the transducer unit 41 in approximately the radial direction by transmitting a rotational motion of the motor in the scanner device 81 to the drive shaft 42 and rotating the housing 412 fixed to the distal end of the drive shaft 42. The ultrasound image obtained here is a transverse image inside the blood vessel. Also, by pulling the whole catheter 1 toward the hand side (proximal direction) and by making the transducer unit 41 move in the lengthwise direction, it is possible to obtain in a scanning manner a 360-degree cross-section image at any desired position in the surrounding tissues extending in the axial direction inside the blood vessel.

The rotor 52 holds, as shown in FIG. 5, the connection pipe 53 and rotates integrally with the male connector 51. The end of the connection pipe 53 opposite the rotor 52 holds the drive shaft 42 in order to transmit rotation of the rotor 52 to the drive shaft 42. The signal line 54 passes through the inside of the connection pipe 53. One end of this signal line 54 is connected to the male connector 51, and the other end passes through the inside of the drive shaft 42 and is connected to the transducer unit 41. An observation result in the transducer unit 41 is transmitted to the external drive apparatus 80 through the male connector 51, is subjected to appropriate processing, and is displayed as an image.

Into the hub main body 55, a portion of the inner tube 312 is fitted by insertion and the anti-kink protector 57 is arranged to surround the inner tube 312 and the hub main body 55. The anti-kink protector 57 is formed by a material having a medium hardness that is between the hardness of the inner tube 312 and the hardness of the hub main body 55, and it is possible for the anti-kink protector 57 to inhibit or prevent the bending, twisting and the like of the inner tube 312 caused by a rapid change in rigidity at a region in which the inner tube 312 is exposed from the hub main body 55.

In the inside of the inner tube 312, there is arranged the support tube 7 between the drive shaft 42 and the inner tube 312. This support tube 7 is opened at the end portion on the hub 31 side (proximal end) and is not held by anything. That is, the proximal end is an unsupported free end 71. The support tube 7 extends to the outer tube 331 shown in FIG. 6.

Referring to FIG. 6, the unit connector 32 includes a unit connector main body 61, a sealing member 62, a cover member 63 and a packing 64. It is also possible for the unit connector main body 61 and the cover member 63 to be made as a single molded component.

The outer tube 331 attached to the relay connector 33 is inserted into or positioned in the unit connector main body 61, and the inner tube 312 extending from the hub 31 is inserted into or positioned inside this outer tube 331. The sealing member 62 holds the packing 64 in combination with the unit connector main body 61. The cover member 63 holds the outer tube 331 in combination with the unit connector main body 61.

Also, with respect to the inner tube 312 extending from the hub 31, a stopper 313 is formed at the distal end thereof, so that when the hub 31 is pulled out to the maximum extent, more specifically even when the inner tube 312 is pulled out from the outer tube 331 to the maximum extent, it is possible to avoid a phenomenon in which the stopper 313 is engaged with the inner wall of the unit connector main body 61 whereby the inner tube 312 is pulled out from the unit connector 32.

The relay connector 33 includes, as shown in FIG. 1 and FIG. 6, an outer tube hold portion 65 and a relay connector main body 66. The outer tube hold portion 65 holds the outer tube 331. Also, the proximal end portion of the catheter main body 2 is interlocked with the inner surface of the outer tube hold portion 65, and there is formed a path for introducing the drive shaft 42 passing through from the outer tube 331 into the catheter main body 2. It is also possible, by further inserting a plurality of tubes into the inside of this path, to prevent buckling or the like of the drive shaft 42.

The support tube 7 is fixed on the inner wall of an exit member 332 through which the drive shaft 42 of the outer tube hold portion 65 passes. This support tube 7 extends toward the inside of the inner tube 312 extending from the hub 31. Consequently, when the inner tube 312 is pressed into the outer tube 331, the support tube 7 is pressed into the inner tube 312 in a direction opposite to the direction of aforesaid pressing. When the inner tube 312 is pressed in or pulled out with respect to the outer tube 331, it happens that also the support tube 7 is relatively pressed in or pulled out with respect to the inner tube 312 from the opposite direction, so that even if a bending force arises at the drive shaft 42, the bending force is suppressed by the support tube 7, and so it is possible to inhibit or prevent bending or the like.

The relay connector main body 66 is an anti-kink protector interlocked with the distal side of the outer tube hold portion 65 and inhibits or prevents the bending (kink) of the catheter main body 2 caused by a rapid change in rigidity while covering and protecting the outer surface of the catheter main body 2.

Referring to FIG. 6 and FIG. 7, the bias member 72 is arranged in covering relation to the support tube 7 and is also configured and positioned to apply a bias (tensile) force between the inner tube 312 and the relay connector 33. The bias member 72 is, for example, constituted by a tensile coil spring. In FIG. 6, there is shown an initial state in which the bias member 72 is contracted and in FIG. 7, there is shown a state in which the bias member 72 is expanded. One end of the bias member (tensile coil spring) 72 is fixed to the inner tube 312 and the other end of the bias member 72 is fixed to the relay connector 33 (the exit member 332, the outer tube 331).

The description below describes the steering of the catheter 1 when observing the living body lumen.

Prior to the insertion of the catheter main body 2 of the catheter 1 into the living body lumen, priming operation is performed for filling the inside of the catheter 1 with physiological saline solution. Carrying out this priming operation removes air inside the catheter 1 and thus helps prevent air from entering the inside of the living body lumen such as a blood vessel or the like.

Next, as shown in FIG. 8, the catheter 1 is interlocked with the external drive apparatus 80. More specifically, the male connector 51 is interlocked with the female connector of the external drive apparatus 80 and the recess portion 61a of the unit connector main body 61 is fitted into the catheter support portion 822 of the external drive apparatus 80.

Next, the hub 31 is pressed-in and there is obtained a state in which the inner tube 312 is pressed to the maximum extent into the outer tube 331 (see FIG. 3). In this state, the catheter main body 2 is to be inserted into the inside of the body and then the insertion operation is stopped after the distal end of the catheter main body 2 passes the target lesion.

For example, in a case in which the catheter 1 is inserted into a coronary artery blood vessel of a heart, a guiding catheter is inserted into the inside of the body before the insertion of the catheter 1 and concurrently, the guiding catheter is indwelled at an entrance of the coronary artery blood vessel.

Thereafter, the guide wire 25 is inserted to a target portion of the coronary artery blood vessel through the guiding catheter. Then, the catheter 1 is inserted along the guide wire 25 in the inside of the guiding catheter. At the proximal end of the guiding catheter, there is interlocked a Y-shaped Y connector having a main body portion which communicates with the guiding catheter coaxially and a side port branched from this main body portion, and a sealing property of a clearance portion between the catheter 1 and the guiding catheter is secured by the Y connector.

Next, the catheter 1 is made to reach the target region inside the living body lumen and thereafter, the position of the catheter main body 2 is fixed. In this state, by performing a pullback operation while rotating the drive shaft 42, it becomes possible to obtain an image in the axial direction of the living body-lumen (see FIG. 4).

It is possible for the pullback operation to be carried out by operating the axial direction moving device 82 connected to the rear end portion of the catheter 1 by way of the control unit 83. The obtained data are subjected to digital processing at the control unit 83 and thereafter, displayed on the display unit 84 as image data.

Operational effects and advantages of this embodiment disclosed by way of example will now be described.

The catheter 1 of this embodiment, includes the catheter main body 2, the drive shaft 42 and the bias member 72 for applying a biasing force to the drive shaft 42 to move the drive shaft 42 forward toward the distal side so that even in a case in which the drive shaft 42 is moved backward toward the proximal side erroneously, release of the backward movement of the drive shaft 42 allows the drive shaft 42 to move forward toward the distal side by a restitutive force which the bias member 72 biases or applies. Consequently, it becomes possible to inhibit or prevent the drive shaft 42 from getting into a state in which it remains in backward movement inside the catheter main body 2 and it becomes possible to inhibit or prevent a defect such as a kink or the like from occurring at the catheter main body 2 when a catheter operation is carried out.

It is also possible during transportation to inhibit or prevent a phenomenon in which a pullback occurs by the vibration or the like associated with the transportation. Consequently, it is possible to simplify the packing.

Also, in case of priming the working lumen 23, even when the drive shaft 42 is pulled back by the influence of the priming operation, it restorably moves toward the distal side automatically. Consequently, it becomes possible to inhibit or prevent a defect such as a kink or the like from occurring at the catheter main body 2.

The drive shaft 42 moves backward toward the proximal side thereof against the force biased or applied by the bias member 72 at the time of detecting the inspection wave by the transducer unit 41, so that it never happens that the detection of the inspection wave is disturbed.

The catheter 1 includes, further, the hub 31, the inner tube 312, the relay connector 33 and the support tube 7, and the bias member 72 is arranged so as to cover the support tube 7 and also, so as to apply a bias (tensile) force between the inner tube 312 and the relay connector 33. Thus, it is possible for the bias member 72 to apply a biasing force to the drive shaft 42 for moving the drive shaft 42 forward toward the distal end or direction. Also, since the bias member 72 covers the support tube 7, it is possible to expect also an effect of preventing the bending of the support tube 7.

The present invention is not limited by the example of the embodiment described above and illustrated in the drawing figures, and can be changed variously within the scope of the claims. For example, in the aforementioned embodiment, it was explained with respect to a case in which diagnosis is carried out by utilizing an intravascular ultrasound (IVUS) image diagnosis catheter, but it can also be applied to another catheter for diagnosis. For example, as an imaging apparatus for diagnosis, an optical coherent tomography diagnostic apparatus (OCT: Optical Coherence Tomography) is also coming to be utilized. The optical coherent tomography diagnostic apparatus is an apparatus in which low coherent light ejected or emitted from a light source is divided into measurement light and reference light and thereafter, reflection light from a measurement target or backside scattered light, which is produced when this measurement light is irradiated to the measurement target, is combined with the reference light and a tomographic image is obtained based on the intensity of coherent light between this reflection light and the reference light, and a catheter incorporating an imaging core incorporating an optical fiber whose distal end is equipped with an optical lens and an optical mirror is inserted into a blood vessel, and light is irradiated to the inside of the blood vessel while performing radial scanning of the imaging core arranged on the distal side of the optical fiber and cross-section images of the blood vessel are visualized based on the reflected light from biological tissue. In other words, in a case in which the disclosure here is applied to an optical coherent tomography diagnostic apparatus, an imaging core is made to incorporate an optical fiber for carrying out transmission & reception of an optical signal and at the distal end of the optical fiber, there is provided a reflection portion for refracting the traveling direction of the light in the diameter direction of the catheter. Also, for the optical coherent tomography diagnostic apparatus, it is possible to use FD-OCT measurement for obtaining a reflection light intensity distribution corresponding to the depth position by measuring the coherent light intensity for every light spectrum component without changing the optical path lengths of reference light and signal light with the use of a wavelength sweep type light source and by applying, with a computer, a frequency analysis typified by Fourier transform to the spectrum interference intensity signal obtained here.

In the intravascular ultrasound (IVUS) image diagnosis catheter, it becomes possible, by performing a pullback operation while rotating the drive shaft 42, to obtain an image in the axial direction of the living body-lumen and on the other hand, if it is an optical coherence type imaging apparatus for diagnosis using near infrared light, by flashing the inside of the blood vessel with a physiological salt solution containing a contrast agent or the like before the pullback through a side port of the Y connector interlocked with the proximal end of the guiding catheter, it becomes possible to obtain an image of the blood vessel in a state in which the blood is excluded. Therefore, not only ultrasound but also anything applicable for detecting light, magnetic field, sound or the like can be applied as the inspection wave.

Figure 9:
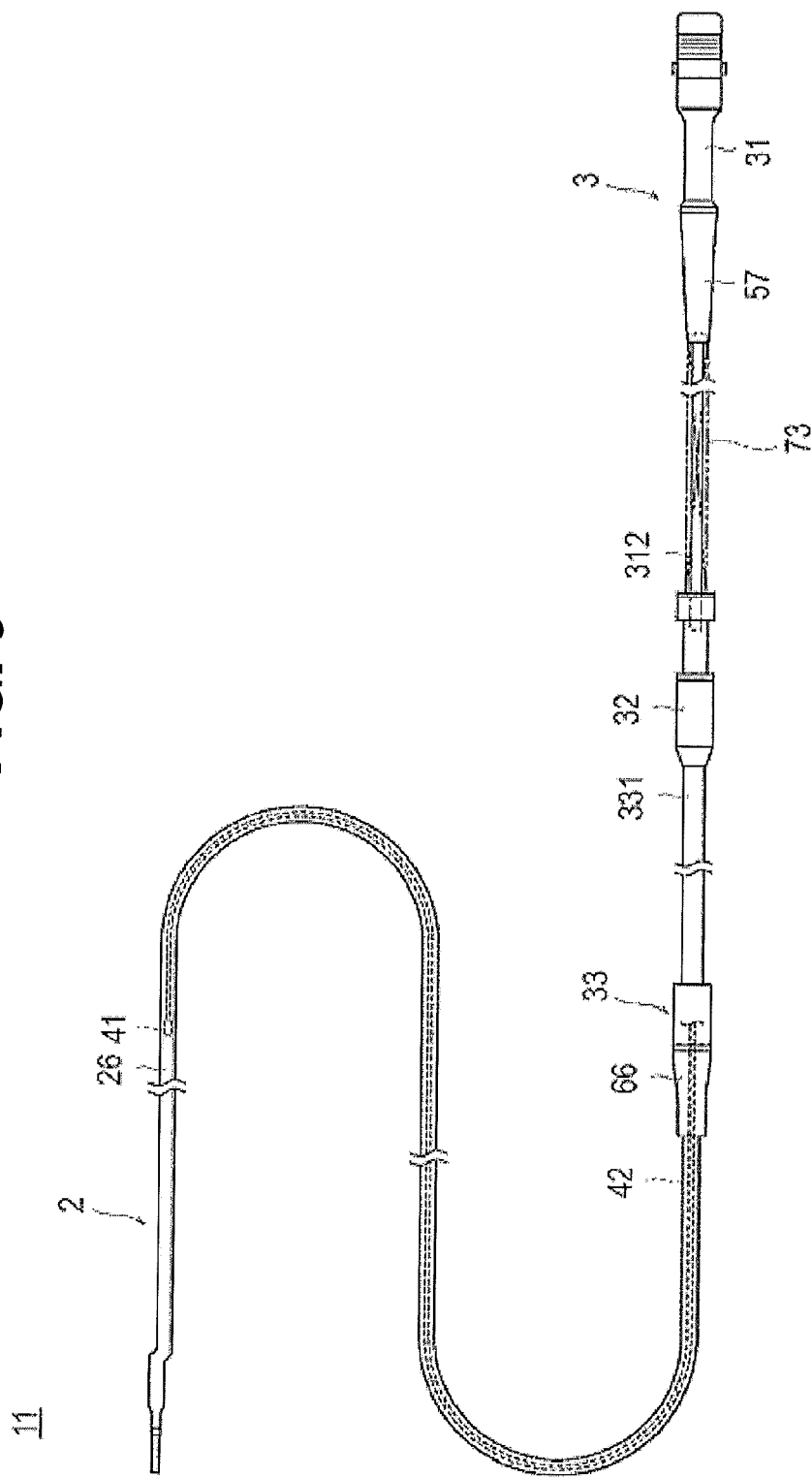
FIG. 9 is a schematic constitutional view showing a catheter of a second exemplified embodiment.

FIG. 9 illustrates a catheter 11 according to a second embodiment disclosed by way of example. Features in this embodiment that are the same as in the first embodiment described above are identified by identical reference numerals and an explanation of such features is not repeated here.

The catheter 11 of the second embodiment, similar to the first embodiment, includes a catheter main body 2, a drive shaft 42 and a bias member 73 for applying a biasing force onto the drive shaft 42 for moving the drive shaft 42 forward toward the distal side thereof. The catheter 11 of the second embodiment further includes a hub 31, an inner tube 312 (an example of a tubular body) and a unit connector 32 connected to the catheter main body 2 (an example of a second connector unit). Then, in the second embodiment, the bias member 73 covers the inner tube 312 and also applies a bias (tensile) force between the hub 31 and the unit connector 32. The bias member 73 is constituted, for example, by a tensile coil spring.

With respect to the bias member 73 in the second embodiment, similarly to the first embodiment, even in a case in which the drive shaft 42 is moved backward toward the proximal side erroneously, when the backward movement of the drive shaft 42 is released, the drive shaft 42 moves forward toward the distal side by a restitutive force which the bias member 73 applies or biases. Consequently, it becomes possible to inhibit or prevent the drive shaft 42 from getting into a state in which it remains in backward movement inside the catheter main body 2 and it becomes possible to inhibit or prevent a defect such as a kinking or the like from occurring at the catheter main body 2 when a catheter operation is carried out.

Also, during transportation, it is possible to inhibit or prevent a phenomenon in which a pullback occurs by the vibration or the like associated with the transportation. Consequently, it is possible to simplify the packing.

Also, in case of carrying out the priming of the working lumen 23, even when the drive shaft 42 is pulled back by the influence of the priming operation, it restorably moves toward the distal side automatically. Consequently, it becomes possible to inhibit or prevent a defect such as a kink or the like from occurring at the catheter main body 2.

The catheter 11 includes, further, the hub 31, the inner tube 312 and the unit connector 32, and the bias member 73 covers the inner tube 312 and also applies a bias (tensile) force between the hub 31 and the unit connector 32. Thus, it is possible for the bias member 73 to apply a bias force to the drive shaft 42 for moving the drive shaft 42 forward toward the distal side. Also, since the bias member 73 covers the inner tube 312, it is possible to expect also an effect of inhibiting or preventing the bending of the inner tube 312.

The detailed description above describes a catheter and manner of using the catheter. The invention is not limited, however, to the precise embodiments and variations described above and illustrated in the drawing figures. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A catheter positionable in a living body lumen to transmit and receive inspection waves at tissue in the living body lumen to form an image of the tissue, the catheter comprising:

a catheter main body;
a detector positioned in the catheter and configured to detect the inspection waves and output signals based on the inspection waves detected by the detector;
the catheter main body possessing a distal end portion at which is located a window portion configured to permit the inspection waves to pass through to be detected by the detector, the detector being axially positionable in the catheter main body to detect the inspection waves passing through the window portion;
a signal line connected to the detector to transmit the signals from the detector;
a drive shaft positioned in the catheter main body and operatively connectable to an external drive apparatus to move the drive shaft rotationally and axially in a distal direction and a proximal direction, the drive shaft possessing a distal end to which the detector is fixed so that the detector moves axially and rotationally together with the drive shaft;
a tube assembly comprising of at least one tube through which a proximal end of the drive shaft passes; and
a bias member positioned radially outwardly of a tube of the tube assembly, wherein the bias member is configured to bias the drive shaft in the distal direction and further configured to automatically move the drive shaft towards the distal direction if the drive shaft is unintendedly moved in the proximal direction.

2. The catheter according to claim 1, wherein the drive shaft is configured to move backward in a proximal direction against the biasing force applied by the bias member when the detector is detecting the inspection wave.

3. The catheter according to claim 1, further comprising:
a hub fixed to a proximal portion of the drive shaft; and
a first tube body of the tube assembly possessing a proximal portion fixed to the hub and extending in the distal direction from the hub, the drive shaft passing through the first tube body so that the drive shaft and the first tube body axially overlap one another.

4. The catheter according to claim 3, further comprising:
a first connector unit fixed to a proximal end of the catheter main body;
a second tube body of the tube assembly possessing a distal portion fixed to the first connector unit and extending toward the proximal direction from the first connector unit, the drive shaft passing through the second tube body from a proximal end of the second tube body to a distal end of the second tube body so that the drive shaft and the second tube body axially overlap one another.

5. The catheter according to claim 4, wherein the second tube body is located radially inwardly of the first tube body and radially outwardly of the drive shaft, and wherein the bias member is positioned radially outwardly of the second tube body and applies a bias force between the first tube body and the first connector unit.

6. The catheter according to claim 1, further comprising:
a hub connected to a proximal portion of the drive shaft;
a tube body of the tube assembly possessing a proximal portion fixed to the hub and extending in the distal direction from the hub, the drive shaft passing through the tube body;
a connector unit connected to the catheter main body; and
the bias member is positioned radially outwardly of the tube body so that the bias member covers the tube body, axially overlaps with the tube body and applies a bias tensile force between the hub and the connector unit.

7. The catheter according to claim 1, further comprising:
a connector unit fixed to the catheter main body;
a tube body of the tube assembly possessing a distal portion fixed to the connector unit and extending toward the proximal direction from the connector unit, the drive shaft passing through the tube body so that the drive shaft and the tube body axially overlap one another.

8. The catheter according to claim 1, further comprising a guide wire insertion portion possessing a through lumen forming a guide wire lumen configured to receive a guide wire.

9. The catheter according to claim 8, wherein the through lumen forming the guide wire lumen is positioned entirely distally of the window portion.

10. The catheter according to claim 1, further comprising a hub fixed to a proximal portion of the drive shaft, the hub comprising a joint and a male connector inside the joint and connectable to a female connector of the external drive apparatus, the signal line being connected to the male connector.

11. A catheter comprising:
a catheter main body provided with a window portion through which an inspection wave passes;
a drive shaft positioned in the catheter main body and axially movable in an advancing direction and a retracting direction, the drive shaft being provided with a detector configured to detect the inspection wave, the detector being located at a distal portion of the drive shaft and spaced in a distal direction from a proximal end of the drive shaft;
a tube assembly comprising of at least one tube through which the proximal end of the drive shaft passes; and
a bias member positioned radially outwardly of a tube of the tube assembly, wherein the bias member is configured to apply a biasing force to the drive shaft to bias the drive shaft forward in the distal direction.

12. The catheter according to claim 11, wherein the drive shaft is configured to move backward in a proximal direction against the biasing force applied by the bias member at the time of detecting the inspection wave by the detector.

13. The catheter according to claim 12, further comprising:
a hub connected to a proximal portion of the drive shaft;
a first tube body of the tube assembly possessing a proximal portion fixed to the hub and extending in the distal direction from the hub, the drive shaft passing through the first tube body;
a first connector unit connected to the catheter main body;
a second tube body of the tube assembly possessing a distal portion fixed to the first connector unit and extending toward the proximal direction from the first connector unit, the drive shaft passing through the second tube body;
the second tube body being positioned between the first tube body and the drive shaft so that portions of the second tube body, the first tube body and the drive shaft axially overlap one another; and
the bias member covers the second tube body and also applies a bias tensile force between the first tube body and the first connector unit.

14. The catheter according to claim 12, further comprising:
a hub connected to a proximal portion of the drive shaft;
a tube body of the tube assembly possessing a proximal portion fixed to the hub and extending in the distal direction from the hub, the drive shaft passing through the tube body;

a second connector unit connected to the catheter main body; and the bias member covers the tube body and also applies a bias tensile force between the hub and the second connector unit.

15. The catheter according to claim 11, further comprising:

a hub connected to a proximal portion of the drive shaft;

a first tube body of the tube assembly possessing a proximal portion fixed to the hub and extending in the distal direction from the hub, the drive shaft passing through the first tube body;

a first connector unit connected to the catheter main body;

a second tube body of the tube assembly possessing a distal portion fixed to the first connector unit and extending toward the proximal direction from the first connector unit, the drive shaft passing through the second tube body;

the second tube body being positioned between the first tube body and the drive shaft so that portions of the second tube body, the first tube body and the drive shaft axially overlap one another; and the bias member covers the second tube body and also applies a bias tensile force between the first tube body and the first connector unit.

16. The catheter according to claim 11, further comprising:

a hub connected to a proximal portion of the drive shaft;

a tube body of the tube assembly possessing a proximal portion fixed to the hub and extending in the distal direction from the hub, the drive shaft passing through the tube body;

a connector unit connected to the catheter main body; and the bias member covers the tube body and also applies a bias tensile force between the hub and the connector unit.

17. The catheter according to claim 11, further comprising:

a hub connected to a proximal portion of the drive shaft;

an inner tube of the tube assembly possessing a proximal portion fixed to the hub and extending in the distal direction from the hub, the drive shaft passing through the inner tube;

a relay connector connected to the catheter main body; and a support tube of the tube assembly possessing a distal portion fixed on the relay connector and extending in the proximal direction, the drive shaft passing through the support tube and being positioned between the inner tube and the drive shaft.

18. The catheter according to claim 17, wherein the bias member is positioned radially outwardly of the support tube, and the bias member covers the support tube and applies a bias force between the inner tube and the relay connector.

* * * * *